United States Patent [19]

Butler et al.

[11] Patent Number: 4,928,015

[45] Date of Patent: May 22, 1990

[54] MEASURING MULTICOMPONENT CONSTITUENCY OF GAS EMISSION FLOW

[75] Inventors: James W. Butler, Dearborn Heights; Thomas J. Korniski, Livonia; Alex D. Colvin, Oak Park, all of Mich.

[73] Assignee: Ford Motor Company, Dearborn, Mich.

[21] Appl. No.: 252,960

[22] Filed: Oct. 3, 1988

Related U.S. Application Data

[63] Continuation-in-part of Ser. No. 87,171, Aug. 19, 1987, Pat. No. 4,801,805..

[51] Int. Cl.$^5$ ............................................. G01N 21/37
[52] U.S. Cl. ...................................... 250/343; 250/341
[58] Field of Search .................... 250/338.5, 339, 340, 250/341, 343, 352; 356/437, 439

[56] References Cited

U.S. PATENT DOCUMENTS

| | | | |
|---|---|---|---|
| 3,897,154 | 7/1975 | Hawes | 250/345 |
| 4,227,083 | 10/1980 | Sherinski | 280/343 |
| 4,549,080 | 10/1985 | Baskins et al. | 250/343 |
| 4,652,755 | 3/1987 | Solomon et al. | 250/341 |
| 4,829,183 | 5/1989 | McClatchie et al. | 250/352 |

FOREIGN PATENT DOCUMENTS 0209704  1/1987  European Pat. Off. ............ 356/439

*Primary Examiner*—Janice A. Howell
*Assistant Examiner*—T. Nguyen

[57] ABSTRACT

A method is disclosed of making an on-line gas analysis of a multicomponent gas emission flow by (a) continuously sequestering a sample flow from the gas emission flow, which sample flow may be filtered to substantially eliminate solid or liquid particles, diluted to lower its dew point to below room temperature, and changed in either temperature and/or pressure to be substantially the same in temperature and pressure as that of gases used to create reference transmission frequency spectral data employed in step (d); (b) continuously irradiating the sample flow with an electromagnetic radiation beam while modulating the amplitude of infrared frequencies in the audio frequency range of the beam, either prior to or immediately subsequent to irradiation of the sample flow, to produce electromagnetic signals having discernible amplitude variations resulting from spectral interference patterns; (c) detecting and collecting the signals at a sufficiently high rate to substantially completely distinguish between adjacent spectral pattern amplitude peaks without mutual spectral interference and to permit analysis of the signals in real time; and (d) analyzing the signals in real time by (i) mathematically manipulating the signals in accordance with Beer's Law to create reformed background-corrected data, and (ii) applying reference transmission frequency spectral data to the reformed data for each suspected gaseous component to give a linear quantitative measure of the presence of each and every suspected gas component in the gas emission flow.

15 Claims, 8 Drawing Sheets

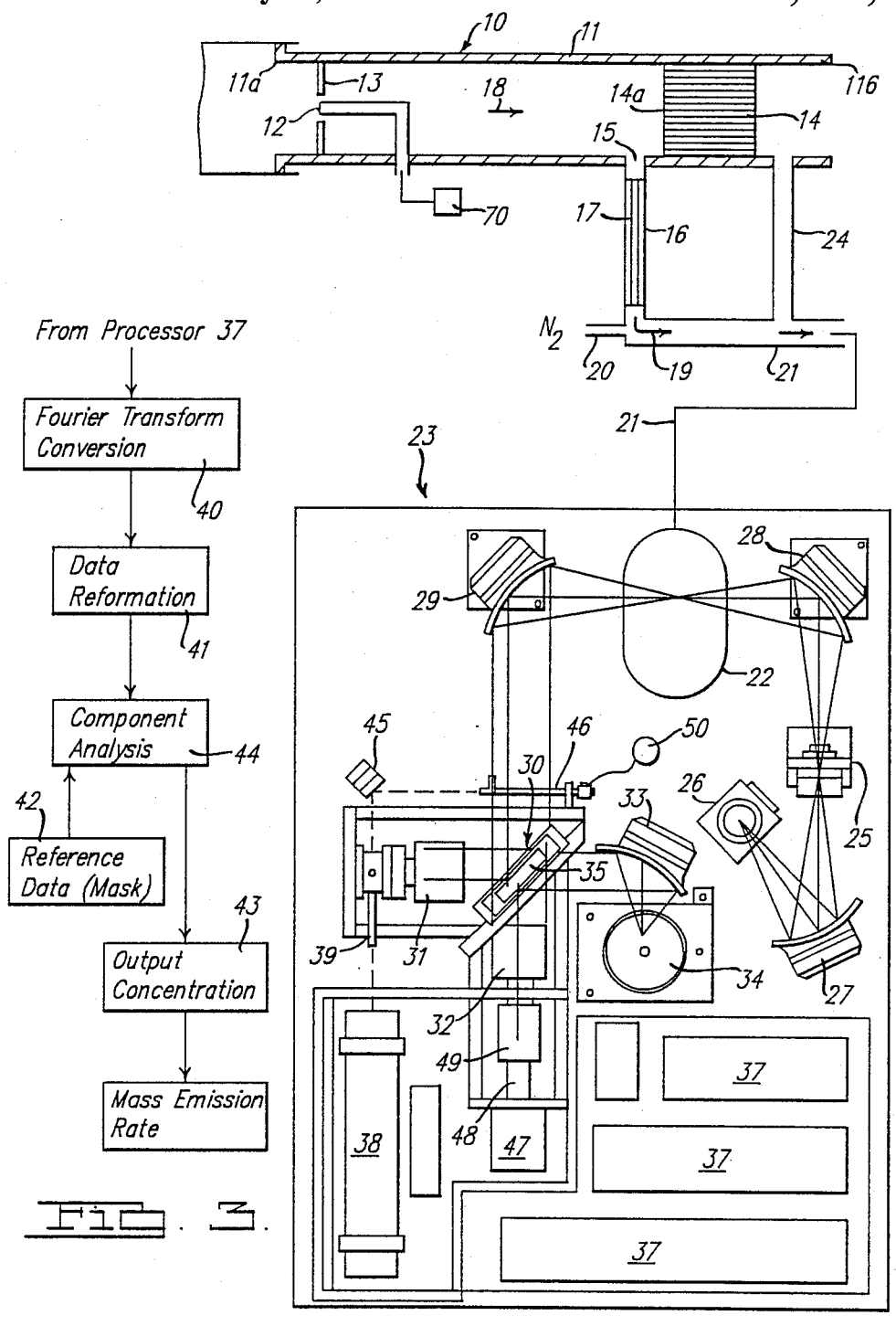

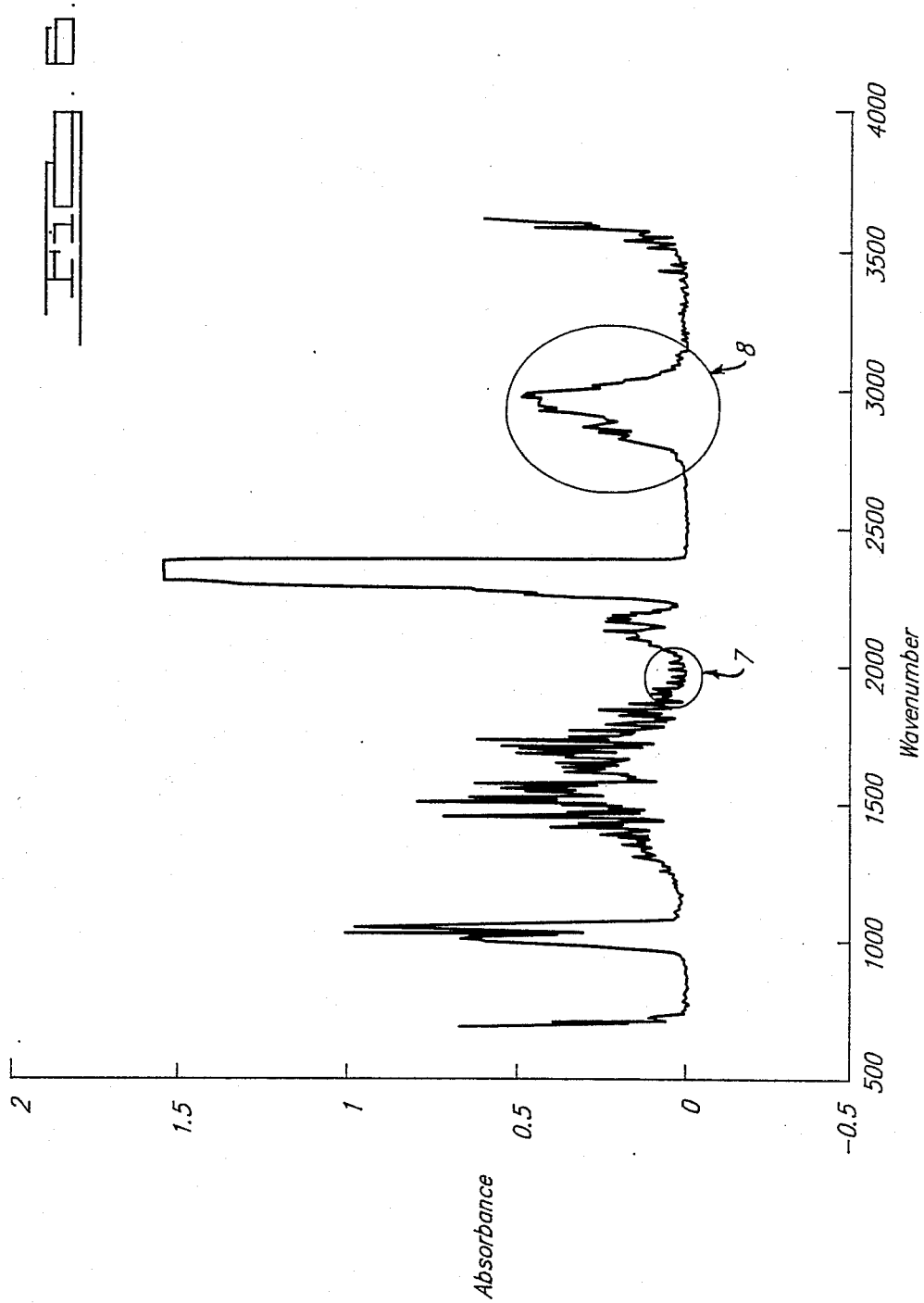

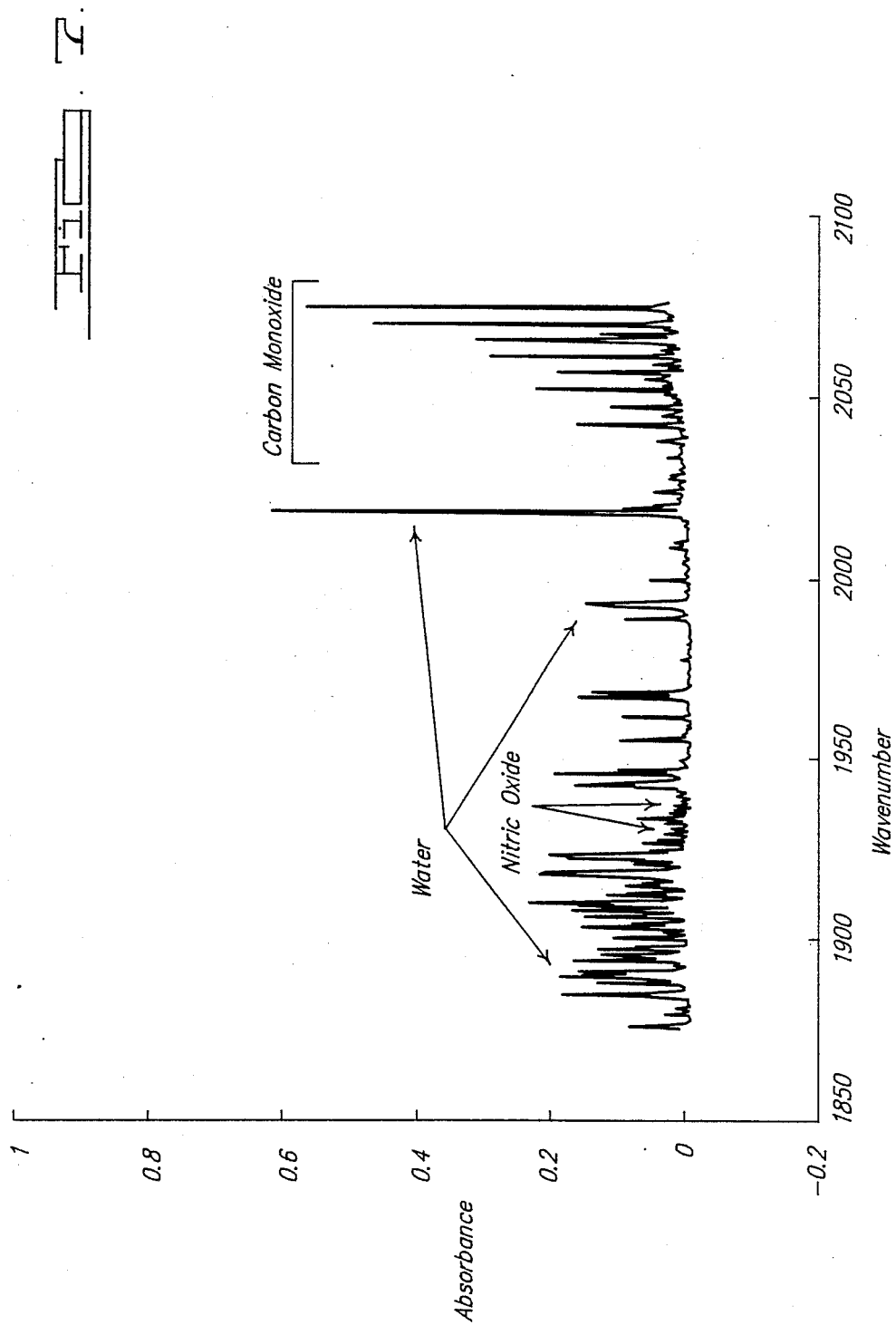

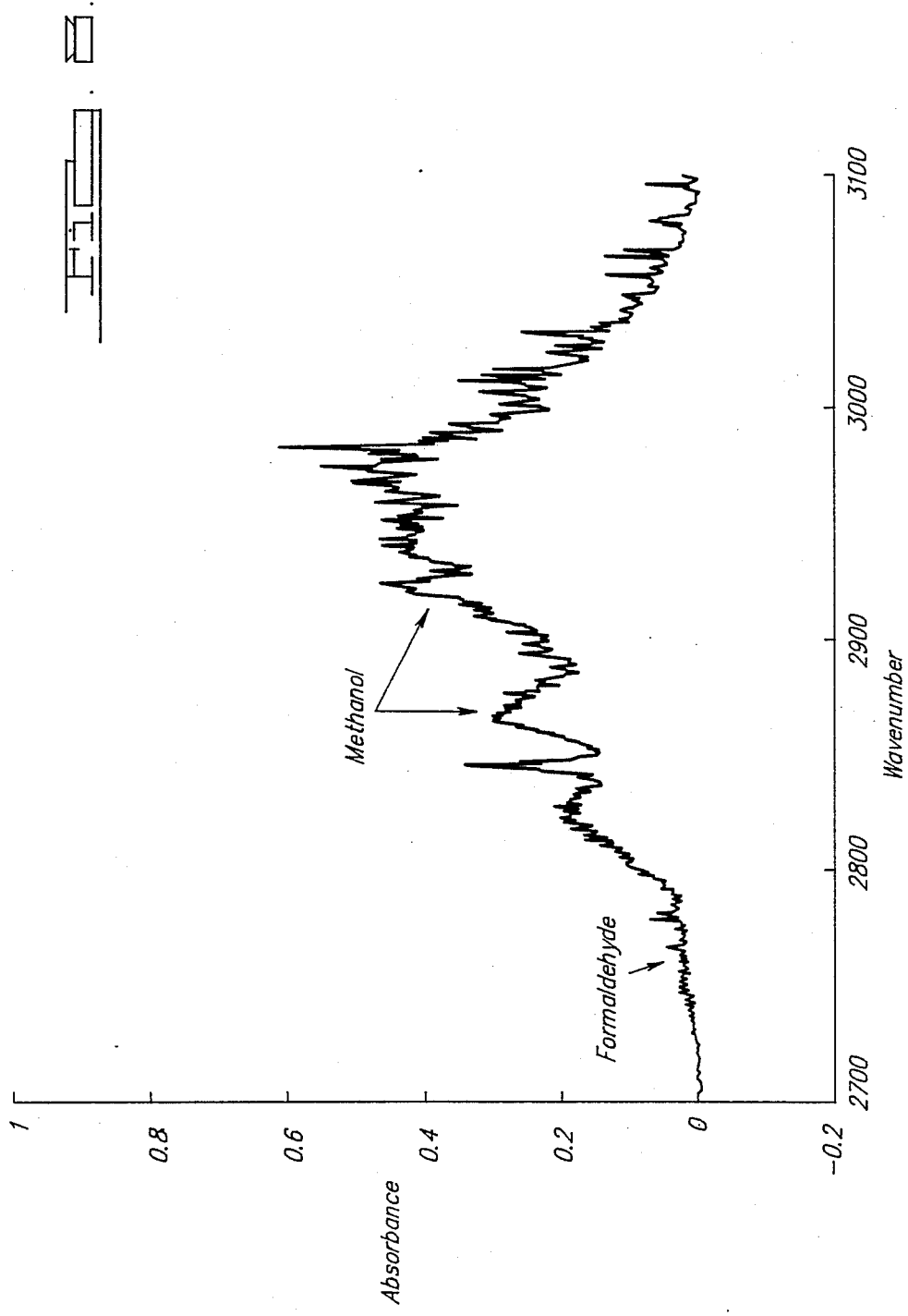

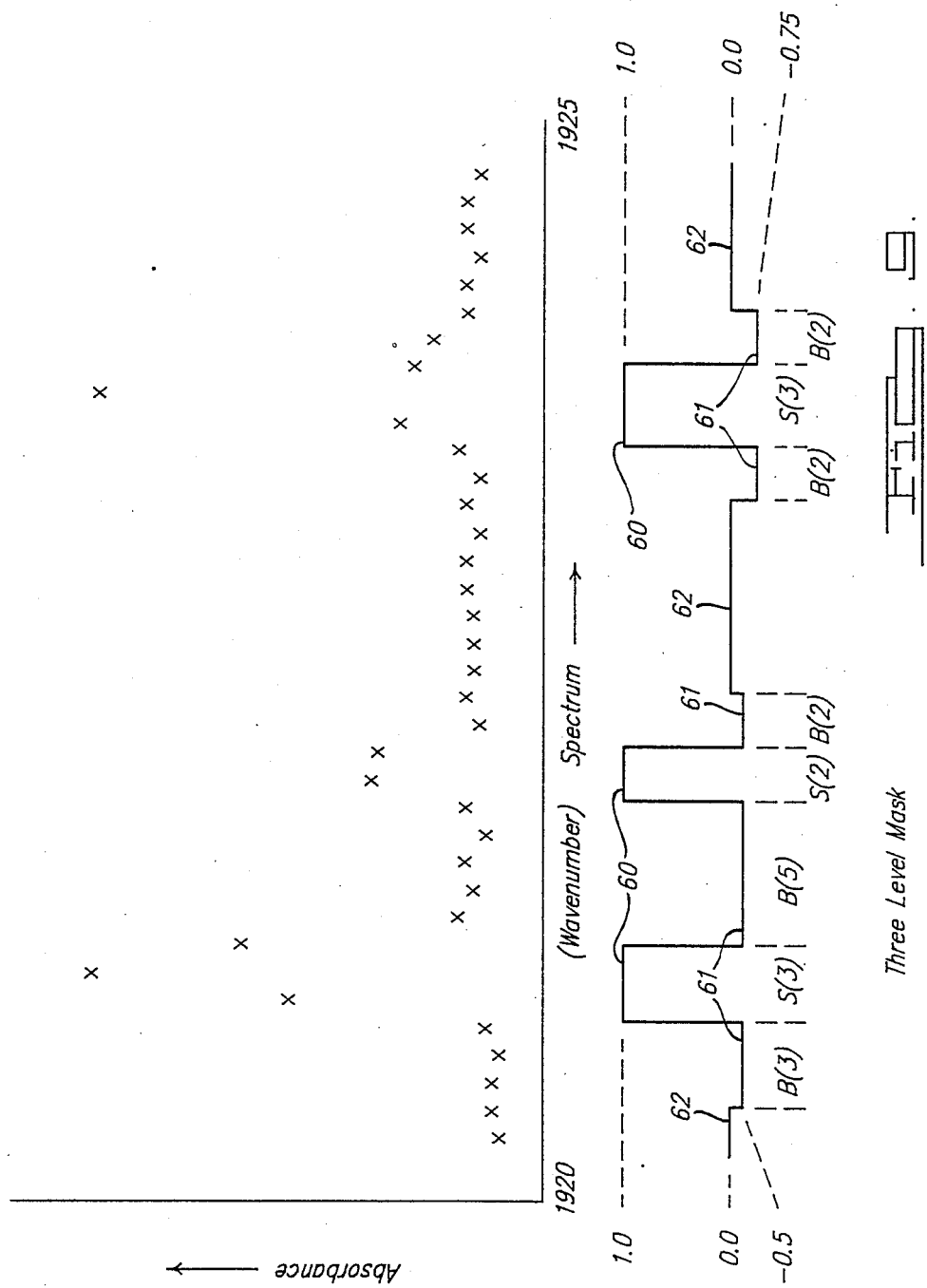

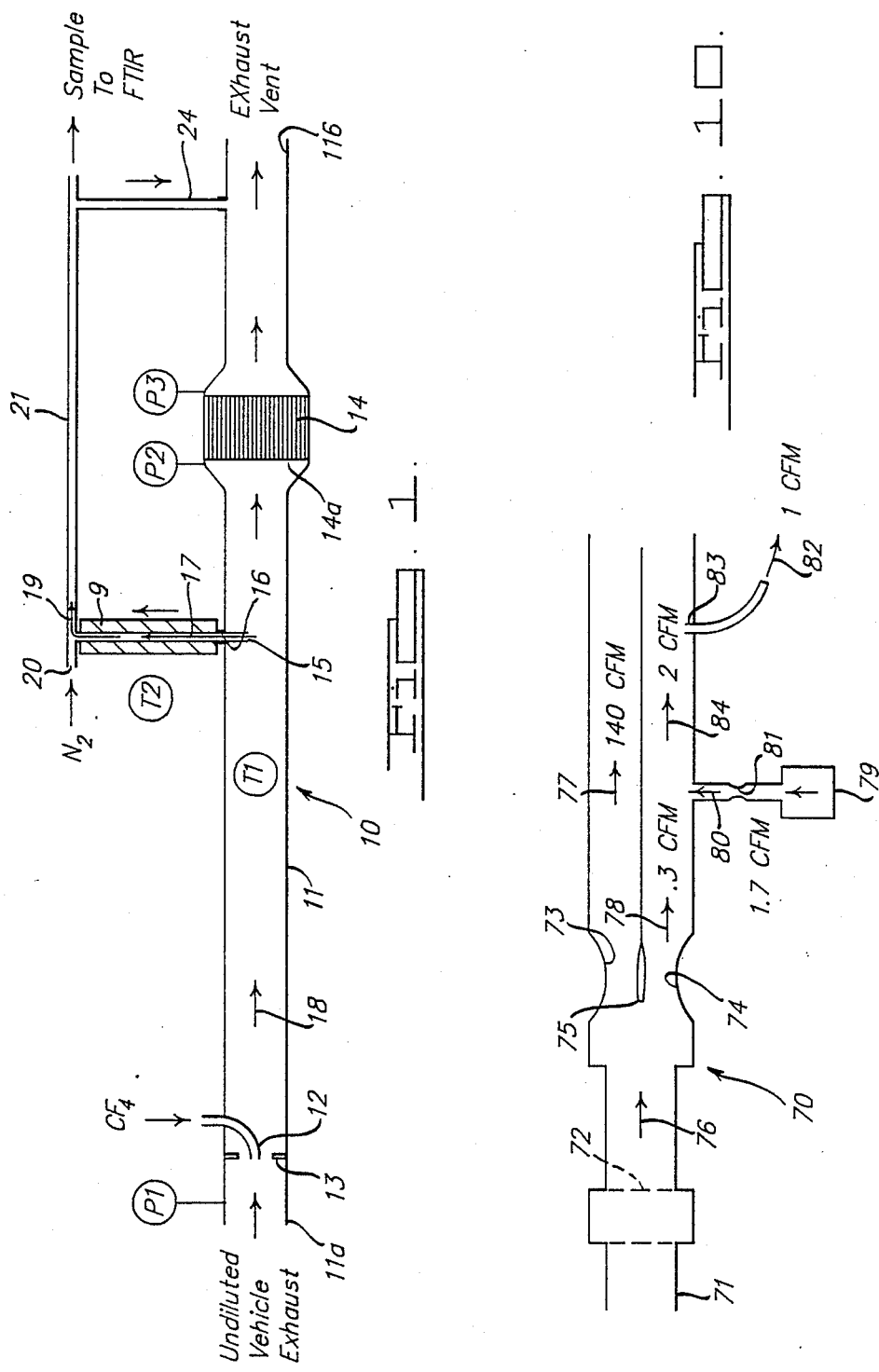

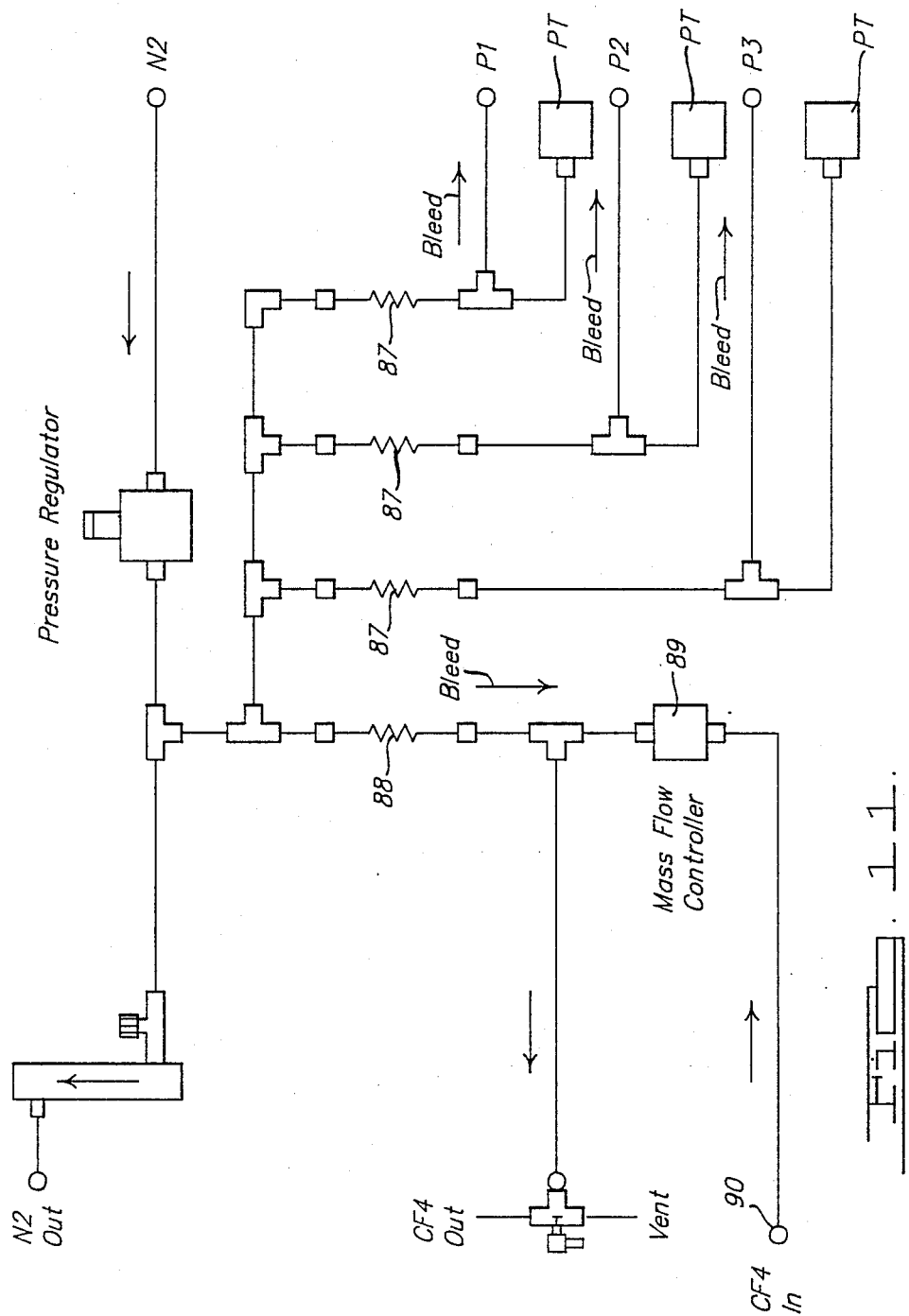

MEASURING MULTICOMPONENT CONSTITUENCY OF GAS EMISSION FLOW

This is a continuation in part application of U.S. Ser. No. 087,171, filed Aug. 19, 1987, entitled "METHOD OF MEASURING MULTICOMPONENT CONSTITUENCY OF GAS EMISSION FLOW."

BACKGROUND OF THE INVENTION

1. Technical Field

This invention relates to the art of gas analysis and, more particularly, to instantaneous on-line analysis of gas flows having multicomponents.

2. Description of the Prior Art

Gas analysis has wide ranging utility, from the measurement of respiration of humans or animals to the measurement of the effluence of combustion chambers, including automotive emissions. Gas analysis has conventionally been accomplished by the use of dilution tubes and by the use of liquids or solids off-line from the flow of gases under analysis. These techniques are inadequate for modern purposes because of the inability to provide instantaneous dynamic information and measure only a single component per technique. These techniques are unable to process increasingly larger volumes of data.

Analyses without liquids or solids have included chemiluminescence, flame ionization, and total hydrocarbon analysis, all without the use of infrared spectroscopy. These modes have proved inadequate because (a) the analysis is of a single component, (b) takes too long, sometimes weeks, (c) the data for separate componenets has no commonality in response time and thus cannot be readily combined, (d) the sensed data suffers from cross-interferences of the added chemicals, and (e) some gaseous compounds cannot be analyzed.

One of the more recent adaptations for gas analysis has been the use of infrared spectroscopy. Although infrared spectroscopy has been used as a quality control technique to obtain information on the composition of chemical products for many years, it has been used essentially off-line and primarily for measurement of nongases. Samples are typically prepared as thin films or solutions and measured in a quality control room with a laboratory instrument. Unfortunately, inherent time delays between actual material production and analytical results can typically range from a few hours to several days, which can result in costly waste and production of unacceptable material. Fourier-transform, infrared spectrometric techniques have been applied to particles suspended in gas flows (see U.S. Pat. No. 4,652,755).

In those prior art applications where infrared spectroscopy was applied to gas analysis, there was no dilution of the gas sampler and therefore the gas itself had to be heated to a temperature in excess of 100° C. to accommodate samples with high water vapor. If other reference information was applied to such detected information, the reference information had to be taken at identical elevated temperatures, which made the entire methodology extremely complex, delicate and difficult to calibrate. In U.S. Pat. No. 4,549,080, filters were used to look at isolated wavelengths, again without dilution.

The task of measuring emissions from vehicles has become increasingly more difficult. Demands for lower detection limits have arisen from the development of more efficient catalytic converters. Greater versatility is required for work with alternate fuels as new and as yet uncharacterized gas species are encountered. In addition to these requirements, a need for more efficient engines with lower emission rates necessitates the development of fast, on-line instrumentation, capable of analysis during transient engine operation. Such new analysis will permit in-depth examination of the combustion process in lieu of the current cumulative information obtained from conventional emissions instrumentations having expensive exhaust handling equipment including constant volume sampling.

Therefore, specific goals of this invention comprise providing an apparatus and method for constant volume sampling of a gas stream, which (i) eliminates the expense, size inefficiency, and inflexibility of large systems used heretofore, (ii) provides more improved accurate testing at normal atmospheric conditions and eliminates false data characteristic of prior sampling systems, (iii) provides a mass emission rate (rather than merely a concentration value of a selected chemical constituent, and (iv) can be used with any chemical sensing system. The elimination of water condensation contamination and the assurance of proportionality of mass flow rate in the sampled gas are most important.

The inventors herein have applied infrared spectroscopy to the on-line analysis of gases, particularly auto emissions. Our earlier work, as described in scientific publication "On-Line Characterization of Vehicle Emissions by FTIR and Mass Spectrometry", Butler et al, SAE Paper #810420 (1981), describes a system for dynamic analysis of vehicle emmissions; the analysis system was comprised of a fourier transform, infrared spectrometer, a quadropole mass spectrometer, and a total hydrocarbon analyzer. Although it allowed on-line measurement of regulated and nonregulated emissions from a steady-state gas stream, the system needed to be calibrated with some difficulty. The three major apparatus components were significantly expensive; but, most importantly, an unusually large size, constant volume sampling apparatus was required for dilution of the sample gas. The speed at which such an integrated system operated was at the rate of three seconds. However, the data was analyzed off-line, rendering an analysis not in real time (while the test is on-going). This introduces an analysis time which is not considered sufficiently fast for the demands of new applications. If the total hydrocarbon analyzer, quadropole mass spectrometer, and constant volume sampling unit could be eliminated, the cost of the system would be significantly reduced. If the remaining components could be improved in response time, the speed of data collection could be increased significantly. Furthermore, if the data could be processed in real time (during the test), the utility of information would be greatly enhanced because adjustments can be made immediately and effects of the adjustments can be seen.

An additional goal of this invention is to provide a combination apparatus of the new sampling apparatus herein with a chemical sensing system of the FTIR type. Such combination apparatus is an on-line measuring apparatus for multicomponent or single component gas emission flows, the apparatus being characterized by improved data collection speed, greater freedom from false or interference data, and is much less costly to fabricate.

SUMMARY OF THE INVENTION

The invention, in a first aspect, is apparatus and method for carrying out constant volume sampling of a gas stream. The apparatus comprises: (a) a channel for conducting the gas stream therethrough between an entrance and exit of such channel; (b) means for extracting a sample flow from the channel which is proportional to the mass flow rate of the stream; and (c) means for diluting the sample flow with an essentially dry, nonreactive gas to lower the dew point of the sample flow to below room temperature. Proportionally sized laminar flow elements may be inserted respectively into the channel and sample flow to ensure proportional mass flow, or streamlined flow foils may be used to restrict and divide the gas stream proportionally to obtain a similar effect in the sample flow. Dilution may be obtained by adding $N_2$, air, or any inert gas, essentially devoid of water, to the extracted sample flow in a volume ratio to the sample flow that will lower its water content and assure lowering the dew point as desired; preferably, $N_2$ gas is used as the diluent and is admitted in a ratio of $N_2$ flow/sample flow of 5:1 to 70:1. A tracer gas of known mass flow may be introduced into the gas stream; its sensed chemical mass flow rate may be used to up-grade or correct any deviations of mass flow rates determined by using pressure to calculate proportional mass flow.

The method of the first aspect for collecting a gas sample to be tested, comprises: (a) conducting a gas emission flow through a passage having a uniform cross-section; (b) extracting a sample flow from the passage and which sample flow is proportional to the known mass flow rate of the emission flow; and (c) diluting the sample flow with a dry, essentially nonreactive gas to lower its dew point to below room temperature. Filtering and/or tracer gases may be employed to improve gas sample for more accurate chemical testing.

The invention, in a second aspect, is a combination apparatus of the sampling device and an FTIR chemical sensor system to provide an on-line gas measurement apparatus. Such apparatus comprises: (a) dilution tube means for sequestering a sample flow from a gas emission flow, said sample flow being proportional to the mass flow rate of the emission flow and diluted to lower its dew point to below room temperature; (b) FTIR apparatus effective to produce electromagnetic signals with discernible amplitude variations resulting from chemical gas species therein after irradiating said sample flow; and (c) means for converting said signals into linear quantities indicative of the presence of distinct chemical gas species. Advantageously, the means for converting signals comprises means for (i) detecting and collecting such signals at a sufficiently high rate to substantially completely distinguish between adjacent spectral amplitudes without mutual spectral interference, and (ii) analyzing the signals in accordance with Beer's Law to create reformed background-corrected data and applying reference transmission frequency spectral data to the reformed data for each suspected gas component to give a linear quantitative measure of the presence of the suspected gas components.

SUMMARY OF THE DRAWINGS

FIG. 1 is a schematic diagram of the sampling device of this invention;

FIG. 2 is a schematic illustration of an FTIR assembly and the sampling device which together display a unique apparatus combination for a total gas analysis measuring system;

FIG. 3 is a flow diagram of certain steps of the FTIR apparatus of FIG. 2;

FIGS. 6, 7, and 8 are graphical representations of absorbance data against wavenumber after applying Beer's Law;

FIG. 9 is a graphical representation of absorbance data plotted against wavenumber showing a spectral mask for $NO_x$ developed from the data points in a spectrum of points from 1920-1925;

FIG. 10 is a schematic diagram of an alternative sampling construction; and

FIG. 11 is a schematic flow diagram of gas flow plumbing controls for connection to the sampling device.

DETAILED DESCRIPTION AND BEST MODE

Obtaining Gas Sample

Figure 4:
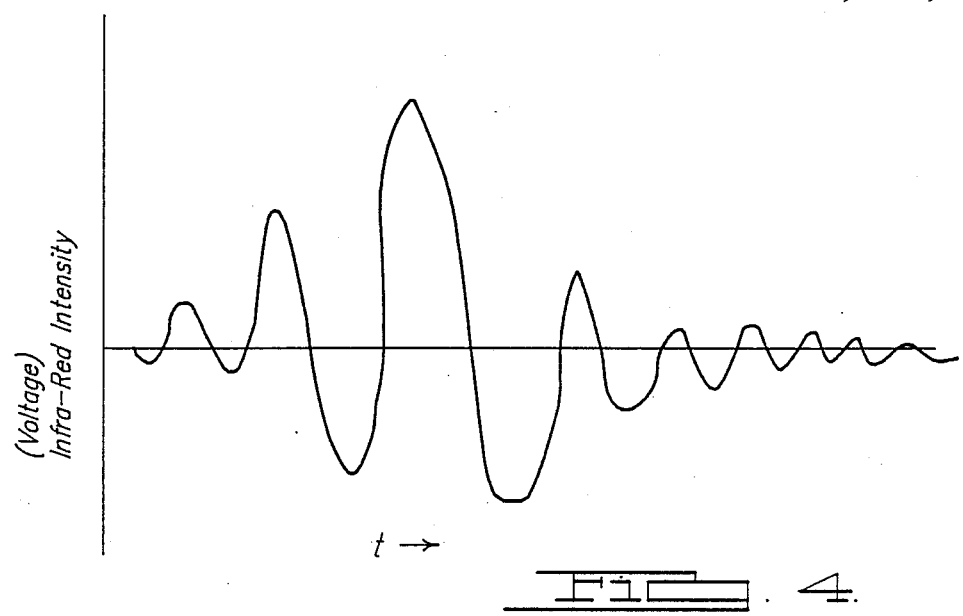
FIG. 4 is a graphical representation of voltage signals plotted against time, such signals eminating from the interferogram.

The first step of the process comprises continuously sequestering a sample of the gas emission flow and affecting the sample flow to make it (i) filtered so as to be substantially devoid of solid or liquid particles, (ii) proportional to the mass flow rate of the gas emission flow, (iii) diluted sufficiently to lower the dew point of the sample flow to below room temperature, and (iv) changed in temperature and pressure to substantially the same temperature and pressure at which reference data was collected. Preferably, the reference data is collected at room temperature and at a pressure of 700 Torr; this will usually necessitate cooling of the sample gas flow to achieve.

As shown in FIG. 1, a sampling device 10 is used to carry out these functions. The device comprises a stainless steel tube 11, preferably having an internal diameter of about 2¼ inches and a length of 3-4 feet. At the entrance or upstream end 11a of such tube (which is connected to the tailpipe or exhaust of an engine), an inlet 12 is located for introduction of a tracer gas, preferably carbon tetrafluoride; the tracer gas is injected at a known rate such as, for example, 3-10 cubic centimeters per minute. The inlet 12 may have a throat diameter of about ⅛ inch and is directed countercurrent to the main exhaust flow and is coplanar with the baffle 13 to achieve thorough mixing. The necessity for the injection of a tracer gas is to enhance the measurement of exhaust mass flow independent of fluctuations in the main emissions flow.

The tracer gas and emissions flow together, pass through the main body of the tube, are mixed, such as by baffle 13, and encounter a main laminar or linear flow restriction element 14 extending across the main flow 18 and across the internal extent of tube 11. The element 14 permits back-pressure to increase in the main flow in response to an increase in mass flow. (Linear flow elements are well known and may contain a number of parallel aligned capillary tubes; the restriction provided by these capillary tubes may typically result in a pressure drop of eight inches of water for an exhaust flow of 100 cfm. A sampling outlet 15 is provided proximate the frontal face 14a of the main linear flow element. The sampling passage 16 also contains a linear flow restriction element 17 extending across the sampling flow 19. A passage 21 carries the sample flow to a cell 22 of an infrared optical apparatus 23. A passage 24 is connected across passage 21 and the outlet end 116 of the tube 11 to set up the same pressure differences to allow the sample to be withdrawn. The downstream pressure of both laminar flow elements 14 and 17 are substantially identical, thus the fraction sampled is proportional to the rate of the conductance of the two laminar flow elements.

The sampled flow 19 is diluted by admission of a dry dilution gas, such as nitrogen, air, or inert gas, having a purity of 99.9%, from an inlet at 20 and admitted, preferably, at a rate of about 30 liters per minute so as to dilute the sample flow in a ratio ranging from about 5:1 to a ratio of 70:1. Dilution is significant because it eliminates condensation and allows the test to take place at substantially atmospheric conditions (preferably 700 Torr), thus minimizing pressure effects on the infrared spectrum and allowing calibration using a preexisting reference data base.

The sampling device eliminates the expense, size inefficiency, and inflexibility of large sampling systems by being short in length and utilizing a proportional mass flow sample from the main flow. As the back pressure at the face 14a of laminar flow element 14 increases, due to an increase in the mass flow of the engine exhaust, the sample flow through 16 will increase proportionally.

The sampling device provides a gas sample for more accurate testing by dilution to lower its dew point below room temperature. Some gas constituents are easily lost during sampling. Certain gas species, such as alcohol, ketones, and aldehydes, are easily dissolved in water. Therefore, water vapor, which is usually present in the engine emissions, will condense during cold start-ups, dissolve such species, and later vaporize during hotter emissions. The chemical sensor will signal a false measurement of such gas species during such transient conditions. Similarly, certain gas species, such as acids, amines, and ammonia, will react quickly with the internal walls of the sampling devices. Such chemical conversion causes the solid product to stick to such internal walls and distort the gas content sampled. By reducing the dew point of the sample gas to below room temperature, no gas species will be lost either by being dissolved in water or chemical reaction with the internal walls.

The amount of diluent can be determined by knowing the water content resulting from combusting a specific fuel at given engine conditions. For example, an unleaded gasoline will usually promote 12.8%±0.5 water content in the combustion emissions. If dew point at ambient conditions requires only 3% water content, then the gas emissions must be reduced from 12.8% to 3%. To conservatively accomplish this, the mass flow of gas emissions must be mixed with a diluting gas in a ratio of about 1:4 to achieve this reduction.

The sampling device has broad ranging utility and can be used with any chemical sensing system including FTIR, nondispersive infrared techniques, chemiluminescence, hydrocarbon detectors, flame ionization techniques, and $SO_2$ or $H_2S$ detectors.

Introduction of the tracer gas eliminates any error in mass flow determinations that may result from a lag in measuring back pressure at the face of laminar flow element 14 and downstream thereof. The gas species to be measured is ratioed by the FTIR system to the tracer component concentration which is also measured by the FTIR. This ratioing provides an instantaneous mass emission of the suspected gas species. Any changes in the dilution are also automatically compensated for by this ratio method. Pressure measurements may be taken by pressure transducers or gauges at locations $P_1$, $P_2$, and $P_3$ as shown in FIG. 1. Such measurements facilitate a check on the determination of a proportional mass flow in the sample flow. To eliminate water vapor or condensation that may interfere with the measurements by the pressure transducers, the dry diluent $N_2$ gas may be bled off and used as a purge with a negligible pressure bias to the transducers PT and to the small sensing ports ($P_1$, $P_2$, and $P_3$). As shown in FIG. 10, this will counter the diffusion of water onto the transducers. The $N_2$ gas is restricted to a bleed by the use of a stainless steel capillary tube 87 at connection of the $N_2$ gas to a pressure transducer PT or by a capillary tube 88 to the mass flow controller 89 for the tracer gas supply 90.

Temperature readings may be taken at $T_1$ and $T_2$ if a heater 9 is needed to heat the sample flow for reducing the dew point to below room temperature. However, heating is not normally needed to effect accurate sampling.

An alternative sampling construction is shown in FIG. 10 and is useful for sampling emission flows from diesel engines containing a large amount of solid particles. The sampling device 70 has channel 71 provided with a filter 72 adjacent its entrance to remove solid particles from the emission stream. A large restriction 73 and a small restriction 74 is used to divide the gas stream 76 to produce two flows, one a large flow 77 and a small flow 78 from which a sample flow is drawn. The equal and constant pressure drop across the restrictions 73 and 74 ensure that the small flow 78 will be a constant fraction of the gas stream 76. The small flow is then diluted with dry air from a supply 79 that injects a flow 80 across a restriction 81 to provide a precalculated dilution of the small flow to a dew point below room temperature. A sample flow 82 is drawn off from the diluted flow 84 at 83. Example flow calculations in cubic feet per minute (cfm) are shown to illustrate the constant volume sampling.

IRRADIATION

The diluted sample flow in the cell 22 is then continuously irradiated by being subjected to an infrared light source to provide test spectral data. This is accomplished by use of an infrared optical apparatus 23, such as shown schematically in FIG. 2, wherein through an optical analysis module arrangement, the infrared light source 26 is directed by mirror 27 through an iris aperture 25 and then again by mirror 28 through the cell 22 of a sampling module containing the diluted sample gas flow. The partially absorbed beam, emerging from cell 22, is directed by mirror 29 into a beam splitter 30. The beam is split at unit 35 into two portions, one portion is reflected by the splitter to traverse a fixed distance or length, into corner-cube mirrors 31 and return to splitter 30 and pass through the splitting unit 35. The other beam part is allowed to pass through unit 35 and traverse a variable length determined by movement of a sliding or stroked corner-cube mirror 32. The corner-cube mirror 32 is moved by a linear magnetic motor 47 operating on a shaft 48 attached to the mirror 38 through a bearing 49. The extent of the mirror cube stroke determines the deviation of the other beam part from the first beam part. The deviated and nondeviated beam parts are recombined by unit 35 to form light signals resulting from spectral interference patterns.

To sense the movement of movable corner-cube mirror 32 and determine when to measure detected signals, a helium-neon laser fringe system 38 is used. The beam emitted from the source at 38 passes through an alignment device 39 associated with fixed corner-cube mirror 31 and thence is directed by mirror 45 to pass into alignment device 46 associated with the movable corner-cube mirror 32. A detector 50 senses the difference or variance from zero alignment between the mirrors and thus senses the location and movement of movable corner-cube mirror 32.

The apparatus 23 differs from conventional grating or prism instruments in that wavelength determination is accomplished by modulating the amplitude of each wavelength of the emitted radiation at its own unique audio range frequency via a scanning Michelson interferometer. The interferometer used was a Mattson SIRIUS 100, equipped with a KBr/Ge beam splitter. The light source was a conventional ceramic glower emitting a broad band infrared radiation, which is close to white light (the latter having all frequencies generally intense). The cell 22 was a Wilks 20 meter variable path cell used in the 14th order resulting in an effective path length of 21.75 meters.

Deviation is used herein to mean the amount of mirror travel or stroke used in splitting off a part of the light beam for developing spectral interference patterns. Spectral interference pattern is used herein to mean the intensity fluctuations imposed on the original beam radiations by the movement of the stroked mirror. An interference pattern results from use of an interferometer giving amplitude modulation of each radiation wavelength at its own unique audio range frequency.

DETECTION

The light signals resulting from spectral interference patterns are directed by mirror 33 to a detector 34 (a liquid nitrogen cooled HgCdTe photoconductor). The spectral emissions are received by the detector on a continuous basis and are converted to an analog voltage. The amplified voltage signals, being a linear measure of the changes in the detector conductivity, are digitized using a computer processor 37. To obtain higher resolution with high volume spectral data eminating from a multicomponent gas emission flow, the detector must detect and collect the light signals (as changes in detector conductivity) at a minimum of 8000 measurements per each centimeter of path length difference and for a minimum of 4 cm of path length difference to create a spectrum of data. This large spectrum of data in a very short interval permits this process to substantially completely distinguish adjacent spectral pattern peaks without mutual spectral interference. A measurement of the detector output voltage is made at uniform spacings during the 4 cm of stroke (at substantially the wavelength of the helium-neon laser). Distinguishing adjacent spectral peaks means employing a long enough corner cube mirror stroke to produce derived spectral patterns with 0.25 cm$^{-1}$ (wave per centimeter) spectral line widths.

The signals were collected during a three second interval by forming an interferogram and writing the interferogram onto computer memory in computer processor 37. The interval (which was three seconds) was determined by the period needed to fully process the spectral data. The detector receives the spectral emission signals as analogue signals per unit of time or interval, and are converted to continuously varying digital signals per unit of time and stored in the computer memory. The signals are received by the detector at a rate of at least 32,000 data points in a three second interval during sweep of the sliding corner cube mirror over a 4 cm path length.

MATHEMATICAL CONVERSION

As represented in the flow diagram of FIG. 3, the ability to detect and record such a high accumulation of data points in such a short period of time is made possible by the use of a multiprocessor computer 40-41-44 having multimemory feed paths. More specifically, the multipath accomplishes the following. While incoming signals are being recorded and stored (i) the previously stored signals can be simultaneously fourier-transformed to yield spectral signals in computer 40, (ii) the transformed signals can be reduced to gaseous component concentration values in computers 41-44, and (iii) the computed values can be displayed on a viewing apparatus. All of this is accomplished in real time.

Figure 5:
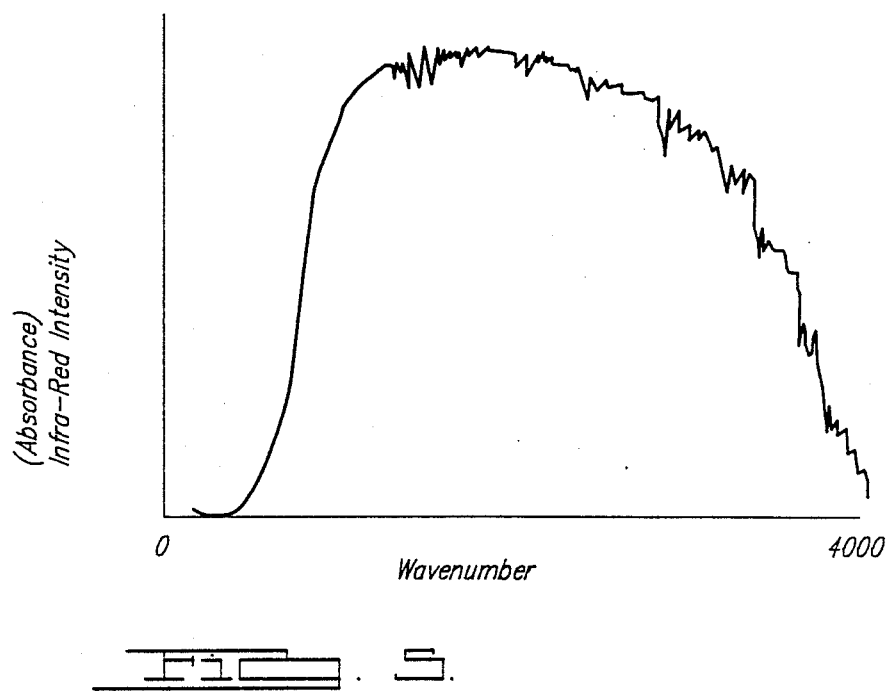
FIG. 5 is a graphical representation of absorbance data plotted against wavenumber eminating from fourier-transform.

In the first stage of mathematical conversion, a spectrum or an interval of the detected signals from spectral interference patterns (interferogram as shown in FIG. 4) is converted to infrared intensity (absorbance) data varying with wavenumber (frequency) as shown in FIG. 5. This is carried out by the use of fourier-transform techniques programmed in computer 40. A detailed description of such techniques used in computer 40 is given in "Introductory Fourier-Transform Spectroscopy", by R. J. Bell, Academic Press, New York (1972). Frequency analysis or fourier analysis of the digitally recorded interferogram leads to the wavelength dependence of the infrared intensity, the infrared spectrum. The use of the fourier-transform spectroscopic method offers great speed advantages when dealing with the very high resolution spectra needed for the quantitative analysis of gas mixtures. FTIR is sometimes used herein to mean the operations carried out by apparatus 23 and computer 40.

To increase the speed of electronic assimilation of such high volume/rate signals, an array processor was used as part of the multiproccessor computer 40. The multiprocessor computer also comprised a Mass comp minicomputer 2M Byte memory, 85M Byte Winchester disks, 1.2M Byte floppy disks, and a 40M Byte magnetic tape system to handle the data processing display and archiving. The software package included a special purpose, fast fourier-transform routine and an extensive set of operator-interactive routines for comparing, combining, displaying, plotting, analyzing and otherwise manipulating spectral files.

The resulting intensity-frequency data (as shown in FIG. 5) was corrected (within electronic computer means 41 for data reformation) for the contribution of room temperature stray radiation by referencing a previously determined room temperature background. A reformed absorbance spectrum was thus generated by calculating the negative logarithm of the ratio of corrected known transmission spectrum of the dilution air background (i.e., taken at 700 Torr and room temperature for the dilution tube air in the cell) to the corrected transmission spectrum of the sample. This eliminates effects of $CO_2$, $H_2O$, and trace hydrocarbons in the ambient air.

The resulting reformed absorbance spectra (as shown in FIG. 6) were then analyzed for components of interest by computer 44. The difficulty of analyzing simply the reformed absorbance data to arrive at a concentration value is demonstrated in FIGS. 7 and 8. It should be noted that for these absorbance spectra, Beer's Law implies that the gas component concentration is linearly related to the spectral line strength. Beer's Law is often recited as:

$$\frac{I}{I_o} = l^{-[\alpha \cdot s(f)]}$$

where
I = intensity of light coming out of absorbance cell
$I_o$ = intensity of light going into absorbance cell
l = gase of natural log, i.e., 2.71828
α = particle density x pathlength
s = absorbance spectrum
f = frequency or wavenumber Only by considerable expertise can the spectral line strengths be identified as a specific gas species. To add the line strengths to arrive at a concentration value is fraught with difficulty. To analyze for components of interest by this invention, reference masks data (contained electronically in computer means 42) are applied to reformed absorbance data (the room temperature corrected spectral information) in computer 44 for each suspected component to render a component concentration.

A mask is explained as follows and by reference to FIG. 9. A linear measure of the concentration of a gas is given by the strength of a line in its true absorbance spectrum. When noise is present in the spectrum, a more reliable measure is provided by summing the strengths of many lines. Such measure is also provided by the height of a narrow line projecting above a broader absorbance feature. The area under the absorbance curve or trace is the measure of the gas species. The method of approximating the area under such curve is speeded up by use of linear algebra in the form of masks. A simulated spectrum or "mask" is prepared consisting of segments 60 made up of 1.0's at spectral positions corresponding to narrow absorbance lines (spectral regions of strong, but not saturating unique absorption for that gas species), segments 61 made up of several small negative fractions at positions surrounding the 1.0's, and segments 62 made up of zero elsewhere. The negative fractions (segments 61) have value (number of 1.0's)/(sum of negatives) and correspond to adjacent localized, nonabsorbing spectral regions. Their purpose is first to establish the average base level above which the narrow line protrudes, and then used to subtract that level from each of the 1.0's. The above sum can then be computed by multiplying together the spectrum from computer 41 (FIG. 4) and the mask, i.e., taking their "dot" product, regarding them to be vectors. This task is accomplished very quickly by the computer's "array" or "vector" processor, particularly if spectral regions where the mask is zero are ignored entirely. The constant or proportionality relating the sum and the concentration of the gas can be determined by employing gases of known concentration, i.e., "standard" gases.

To analyze a mixture of gases, the mask for each species present is applied to the absorbance spectrum of the mixture. For the ideal case in which (mask of gas A) × (spectrum of gas B) = 0 for A = B, the result, upon applying the known constants of proportionality, gives directly the quantitative composition of the sample gas. In practice, the masks are not ideal, but interferences can be accounted for since the response of each mask to the spectrum of each pure gas is known.

The construction of such masks depends upon the availability of a library of reference absorbance spectra for all gases comprising the mixture to be analyzed, in a concentration near that at which they are present in the mix. Each mask is prepared manually with constant referral to the library, the need to maximize response to the subject gas being weighed carefully against introduction of either interferences from other species or unwanted noise. The partial mask was made up of only the essential or unique spectral distinguishing feature points of a known gas species. This step was calibrated to give actual concentration values by applying the partial mask to the spectrum of a carefully selected and prepared standard sample of known concentration.

Individual masks were manually constructed for the best mode by a computer operator from a reference spectrum of a molecule of interest using as guides, in the choice of unique absorption bands, both the spectrum of the exhaust sample to be measured and reference spectra of all other molecules suspected of being present. Separate sets of masks were prepared to handle each of the various combinations of species in concentrations encountered in different experiments. A response matrix was then generated for each set of masks by applying each mask successively to the reference spectrum of each of the molecules represented in that set. Ideally, this would be a unit matrix, but inevitably the masks were imperfect. Such imperfections were eliminated from the final result by multiplication with the inverse of the appropriate response matrix, all in accordance with the prescriptions of linear response theory. The summation value generated by component analysis in computer 44 can be displayed in unit 43.

When a sample is introduced by means of the sampling system shown in FIG. 1, the mass emission rates are preferably obtained by combining the component signal with the signal strength of the carbon tetrafluoride signal and dividing by the mass injection rate of the carbon tetrafluoride tracer.

More specifically, the exhaust mass flow of the engine may be computed by measuring the equivalence ratio as taught in U.S. Pat. No. 4,389,881 and combining this measurement with the hydrogen carbon ratio of the fuel, the oxygen carbon ratio of the fuel, the carbon dioxide fraction in the diluted sample as measured by FTIR, the carbon tetrafluoride mass injection flow, and the carbon tetrafluoride fraction in the diluted exhaust as measured by FTIR. The following illustrates mathematically how this is carried out.

EXHAUST GAS FLOW (BASED ON MINI-CVS)

Lean Case (λ ≧ 1):

$$X = \frac{YD}{W}\left[\frac{N}{4} + \frac{P}{2} + \frac{\lambda}{0.21}\left(1 + \frac{N}{4} - \frac{P}{2}\right)\right]$$

Rich Case (λ < 1):

$$X = \frac{YD}{W}\left[\frac{1 + N/2 + 3.96 \lambda (1 + N/4 - P/2)}{1 - [(1 - \lambda)(1 - N/4 - P/2)] 3/2}\right]$$

where
N = hydrogen/carbon ratio of fuel (no units)
P = oxygen/carbon ratio of fuel (no units)

$\lambda$ = oxygen equivalence of exhaust gas (no units)
Y = $CO_2$ fraction in final diluted sample (measured by FTIR (no units)
D = $CF_4$ tracer flow (STP volume/time)
W = $CF_4$ fraction by FTIR (no units)
X = engine exhaust flow (STP volume/time Alternatively, the mass emission rate is determined by sampling from a dilution tube and by first obtaining the average dilution tube flow (in scfm) for each test by use of a flowmeter 70. This tunnel flow was then converted to liters per three seconds to match the time interval of the FTIR data interval. Based on the tunnel flow and the concentration data, the emissions in milligrams per three second interval are computed for each gaseous component.

Table I shows an actual computer listing of compound concentrations obtained from testing as identified.

TABLE I
Computer Generated Quantitive Analysis
of the Spectrum of a Methanol Fuel FTP Test

| | Compound | Concentration | Estimated Error of Measurement | |
|---|---|---|---|---|
| 1. | $H_2O$ | 0.27 | 0.1% | |
| 2. | $CO_2$ | 0.33 | 0.1% | |
| 3. | COHI | 207.65 | 10.0 | ppm |
| 4. | HCIC | 14.26 | 8.0 | ppmC |
| 5. | NO | 27.74 | 0.3 | ppm |
| 6. | $NO_2LO$ | 3.72 | 0.3 | ppm |
| 7. | $N_2O$ | −0.01 | 0.1 | ppm |
| 8. | HONO | 0.33 | 0.1 | ppm |
| 9. | HCN | −0.03 | 0.2 | ppm |
| 10. | $NH_3Q$ | −0.06 | 0.1 | ppm |
| 11. | $SO_2$ | −0.14 | 0.2 | ppm |
| 12. | $CH_4$ | 0.94 | 0.1 | ppmC |
| 13. | $C_2H_2$ | −0.36 | 0.2 | ppmC |
| 14. | $C_2H_4Q$ | 0.52 | 0.5 | ppmC |
| 15. | $C_2H_6$ | 0.06 | 0.2 | ppmC |
| 16. | $C_3H_6$ | 0.74 | 1.0 | ppmC |
| 17. | $IC_4H_8Q$ | 1.52 | 1.0 | ppmC |
| 18. | $CH_2O$ | 6.93 | 0.1 | ppmC |
| 19. | HCOOH | −0.08 | 0.1 | ppmC |
| 20. | $CH_3OHI$ | 150.98 | 0.1 | ppmC |

Total HC = 175.52 $ppmC_3$
Total NOX = 31.79 ppm

While particular embodiments of the invention have been illustrated and described, it will be noted by those skilled in the art that various changes and modifications may be made without departing from the invention, and it is intended to cover in the appended claims all such modifications and equivalents as fall within the true spirit and scope of the invention.

What is claimed:

1. A gas sampler device, comprising:
  (a) a channel for conducting a gas emission flow therethrough between an entrance and exit of said channel;
  (b) means for extracting a sample flow from said channel adjacent the exit thereof which is proportional to the known mass flow rate of said gas emission flow; and
  (c) means for diluting the sample flow with an inert gas to lower its dew point to below room temperature.

2. The device of claim 1, in which said means of step (b) comprises a laminar flow element extending across said channel and a proportionally sized but similar laminar flow element extending across the sample flow.

3. The device as in claim 1, in which a tracer gas is introduced at a known rate into said gas emission flow adjacent the entrance thereof for comparison to the rate at which it is sensed by a chemical sensor.

4. The device as in claim 3, in which said tracer gas is carbon tetrachloride.

5. The device as in claim 1, in which a filter is placed in said channel to remove solid or liquid particles.

6. The device as in claim 1, in which dividing foils and wall restrictions are used to proportionally divide out a sample flow.

7. An on-line gas measurement apparatus, comprising:
  (a) dilution tube means for sequestering a sample flow from a gas emission flow, said sample flow being diluted to lower its dew point to below room temperature and changed in either temperature and/or pressure to be substantially the same in temperature and pressure as that of gases used to create reference transmission frequency spectral data;
  (b) FTIR apparatus effective to Produce electromagnetic signals with discernible amplitude variations resulting from irradiating said sample flow;
  (c) computer means for (i) detecting and collecting said signals at a sufficiently high rate to substantially completely distinguish between adjacent spectral amplitudes without mutual spectral interference, and (ii) analyzing said signals in accordance with Beer's Law to create reformed background-corrected data and applying reference transmission frequency spectral data to said reformed data for each suspected gas component to give a linear quantitative measure of the presence of each and every suspected gas component in said gas emission flow.

8. The apparatus as in claim 7, in which in step (c), said linear quantitative measure is mass flow.

9. The apparatus as in claim 7, in which said dilution tube means filters said sample flow to substantially eliminate solid or liquid particles.

10. The apparatus as in claim 8, in which a tracer gas is introduced at a known rate into said gas emission flow and is compared to the mass emission flow of such tracer gas detected by the FTIR and computer means to render a correction factor for all linear quantitative measurements made.

11. A method of sampling a gas emission flow for testing, comprising:
  (a) conducting a gas emission flow through a passage having a uniform cross-section;
  (b) extracting a sample flow from the passage which is proportional to the known mass flow rate of the emission flow; and
  (c) diluting the sample flow with a dry essentially nonreactive gas to lower its dew point to below room temperature.

12. A gas sampler device, comprising:
  (a) a channel having a length of four feet or less and an average aspect ratio (length to diameter) of 24 to 9 for conducting a gas emission flow therethrough between an entrance and exit of said channel;
  (b) means for introducing and mixing a tracer gas at a known rate into said gas emission flow adjacent the entrance thereof;
  (c) means extracting a sample flow from the said channel adjacent the exit thereof which is proportional to the known mass flow rate of said gas emission flow; and (d) means for diluting the sample flow with an inert gas to lower its dew point to below room temperature.

13. The device of claim 12, in which said means of (c) comprises a laminar flow element extending across said channel and a similar but proportional laminar flow element extending across the sample flow.

14. The device as in claim 12, in which said tracer gas is carbon tetrachloride.

15. An on-line gas measurement apparatus, comprising:
   (a) dilution tube means for sequestering a sample flow from a gas emission flow, the sample flow being filtered to substantially eliminate solid or liquid particles, diluted to lower its dew point to below room temperature, and changed in either temperature and/or pressure to be substantially the same in temperature and pressure as that of gases used to create reference transmission frequency spectral data;
   (b) FTIR apparatus effective to produce electromagnetic signals with discernible amplitude variations resulting from irradiating said sample flow;
   (c) computer means for (i) detecting and collecting said signals at a sufficiently high rate to substantially completely distinguish between adjacent spectral amplitudes without mutual spectral interference, and (ii) analyzing said signals in accordance with Beer's Law to create reformed background-corrected data and applying reference transmission frequency spectral data to said reformed data for each suspected gas component to give a linear quantitative measure of the presence of each and every suspected gas component in said gas emission flow.

* * * * *